US00PP14439P39

(12) United States Plant Patent
Bjorge et al.

(10) Patent No.: US PP14,439 P3
(45) Date of Patent: Dec. 30, 2003

(54) PEACH TREE NAMED 'FA 42'

(50) Latin Name: *Prunus persica*
Varietal Denomination: FA 42

(75) Inventors: Annette Bjorge, Coloma, MI (US); Randy Bjorge, Coloma, MI (US)

(73) Assignee: International Plant Management, Lawrence, MI (US)

( * ) Notice: Subject to any disclaimer, the term of this patent is extended or adjusted under 35 U.S.C. 154(b) by 152 days.

(21) Appl. No.: 10/004,256

(22) Filed: Nov. 2, 2001

(65) Prior Publication Data

US 2003/0088897 P1 May 8, 2003

(51) Int. Cl.[7] ..... A01H 5/00

(52) U.S. Cl. ..... Plt./198
(58) Field of Search ..... Plt./198

*Primary Examiner*—Bruce R. Campell
*Assistant Examiner*—Susan B. McCormick

(57) ABSTRACT

A new peach variety, *Prunus persica,* (hereinafter referred to as 'FA 42 peach') which was developed in 1981 by Annette and Randy Bjorge in a breeding program at Fruit Acres Farms in Coloma, Mich., having the following combination of unique and desirable features:

1. A substantially large, round fruit with an attractive bright red blush covering 75 to 80% of the fruit at maturity.
2. A fruit maturing late in the season, 7 days after 'Fayette' or 45 days after 'Redhaven'.
3. A fruit with excellent storage and shipping qualities.
4. A fruit with flesh that does not brown when cut.

4 Drawing Sheets

FIELD OF THE INVENTION

A new and distinct variety of peach tree originating as a cross of 'Autumnglo' and 'Fayette' varieties of *Prunus persica* hereinafter referred to as 'FA 42' peach. This variety is unique from its parents because the fruit is both highly colored and round and the tree has good bud and wood hardiness. 'FA 42' ripens later than both parents, 6 days after 'Autumnglo' and 7 days after 'Fayette' with large, 75 to 80% blushed red fruit.

SUMMARY OF THE INVENTION

This new and distinct variety of peach tree was developed in a breeding program in 1981 by Annette and Randy Bjorge of Coloma, Mich. It resulted as a cross of 'Autumnglo' and 'Fayette', both unpatented peach cultivars. The new variety was noticed because it ripened very late in the season with a high color factor and large size.

The new variety was budded on Bailey peach seedling in the summer of 1988 and planted for further testing on Fruit Acres Farms, Coloma, Mich. In the summer of 1992, 'FA 42' was budded on Halford peach seedling. In the spring of 1993, these trees were sent to the following cooperating testers under testing agreements: Rutgers Snyder Research Farm, Pittstown, N.J.; Lee Spencer, Boyertown, Pa.; Adams County Nursery, Aspers, Pa.; Kenneth Kauffman, Bird-in-Hand, Pa.; Thomas Benton, Chester, N.J.; Clemson University, Clemson, S.C.; Arnold Klug, Berrien Center, Mich.; North Carolina State University, Raleigh, N.C.; Rutgers Cooperative Extension, Clayton, N.J.; SW Michigan Research & Extension Center, Benton Harbor, Mich.; and The University Of Arkansas, Clarksville, Ark.

The reports from the cooperating testers showed that the new variety remained true to name and showed considerable commercial promise as a peach for the late harvest season.

COMPARISON TO PRIOR ART

'FA 42' ripens vary late in the commercial peach season with a large sized fruit and a very high degree of red skin color. This contrasts to 'Fayette', (an unpatented selection) which ripens 13 days earlier and is much less highly colored. 'FA 42' ripens 6 days after 'Autumnglo' (an unpatented selection) and is more highly colored with a lighter degree of pubescence. The new variety ripens 6 days after 'Encore' (U.S. Plant Pat. No. 4,572) and has a much higher degree of red skin color. 'FA 42' ripens 15 days after 'PF 27A' (U.S. Plant Pat. No. 9,939). 'FA 42' ripens 2 days after 'Laurol' (U.S. Plant Pat. No. 8,558) and has a bright red skin color contrasting with the orange-red of 'Laurol'. 'FA 42' also has a much greater degree of bud and wood hardiness than 'Laurol'.

BRIEF DESCRIPTION OF THE DRAWINGS

The accompanying photographs show typical specimens of the new variety as depicted in color as nearly true as is reasonably possible in color illustrations of this character. These specimens were obtained at Coloma, Berrien County, Mich.

BOTANICAL DESCRIPTION OF THE PLANT

Figure 1:
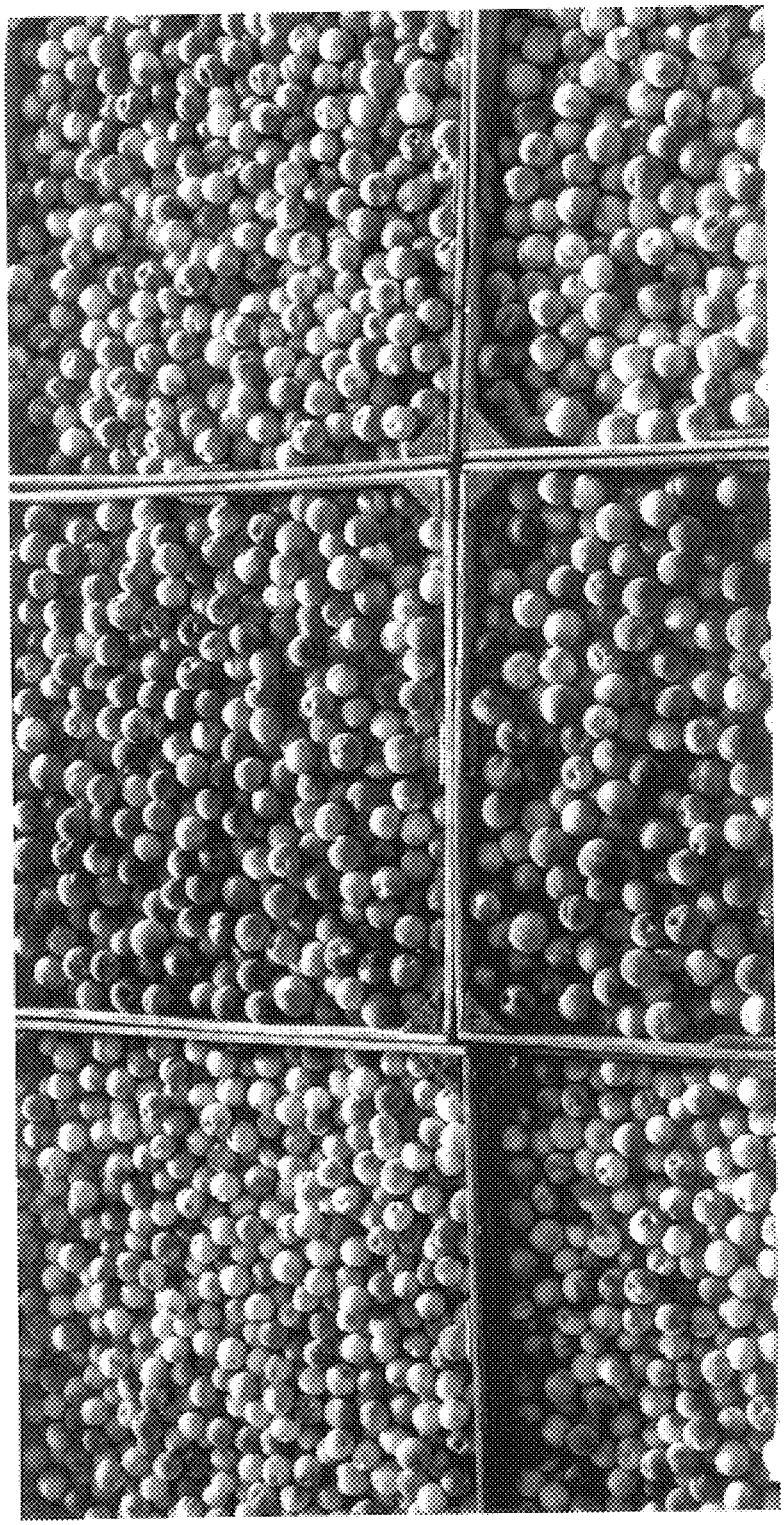
FIG. 1 illustrates the coloration of the fruit of the new variety in comparison with the coloration of 'Fayette' and 'Encore' (U.S. Plant Pat. No. 4,572). 'Encore', picked on September 17, is pictured on the top; 'FA 42' picked on September 24, is pictured in the middle segment; 'Fayette', picked on September 11, is shown in the bottom section. All three varieties were grown on the same farm in Coloma, Berrien County, Mich.
Figure 2:
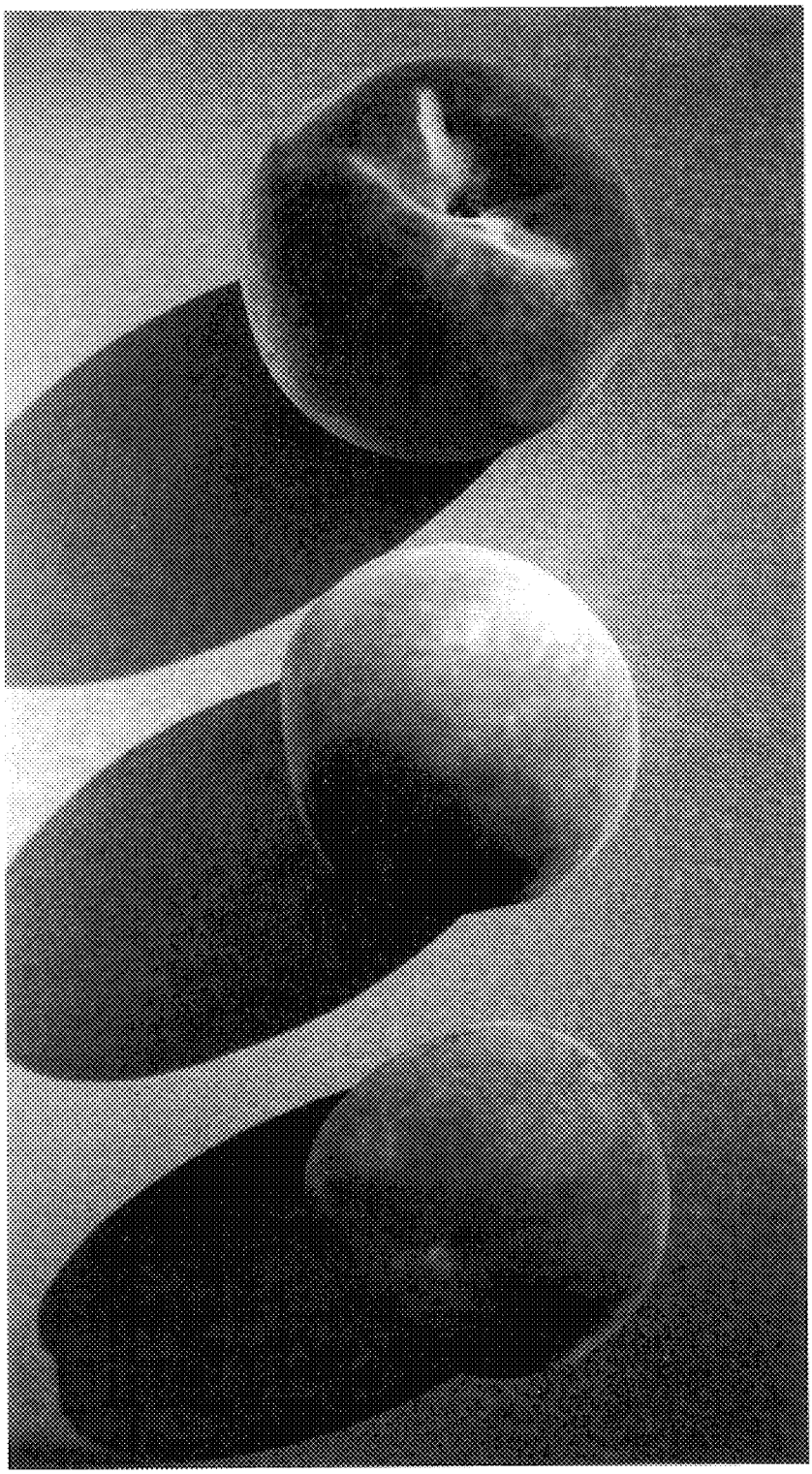
FIG. 2 illustrates several fruit of the new variety at maturity.
Figure 3:
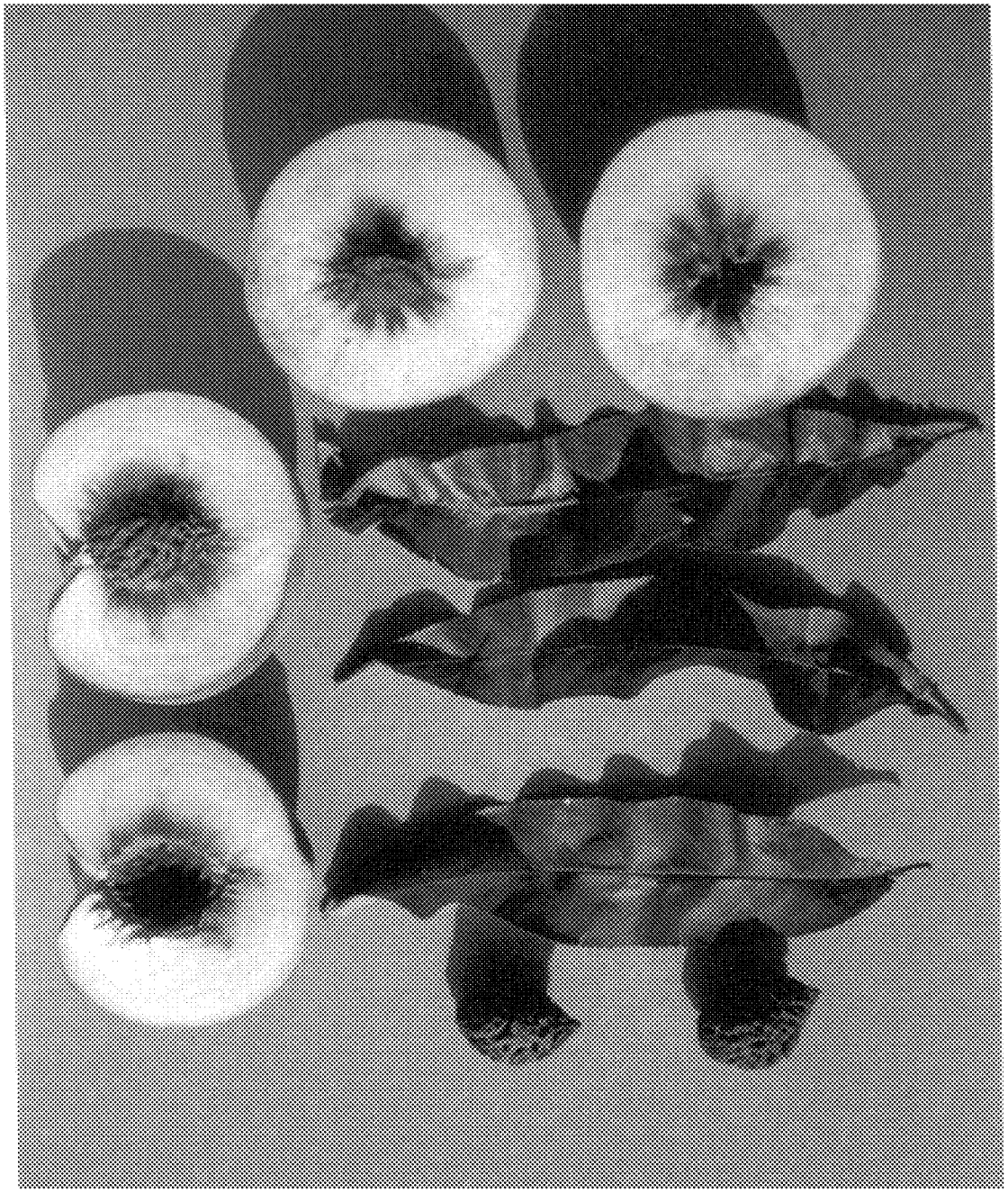
FIG. 3 illustrates sections, leaves, and pits of the new variety at maturity.
Figure 4:
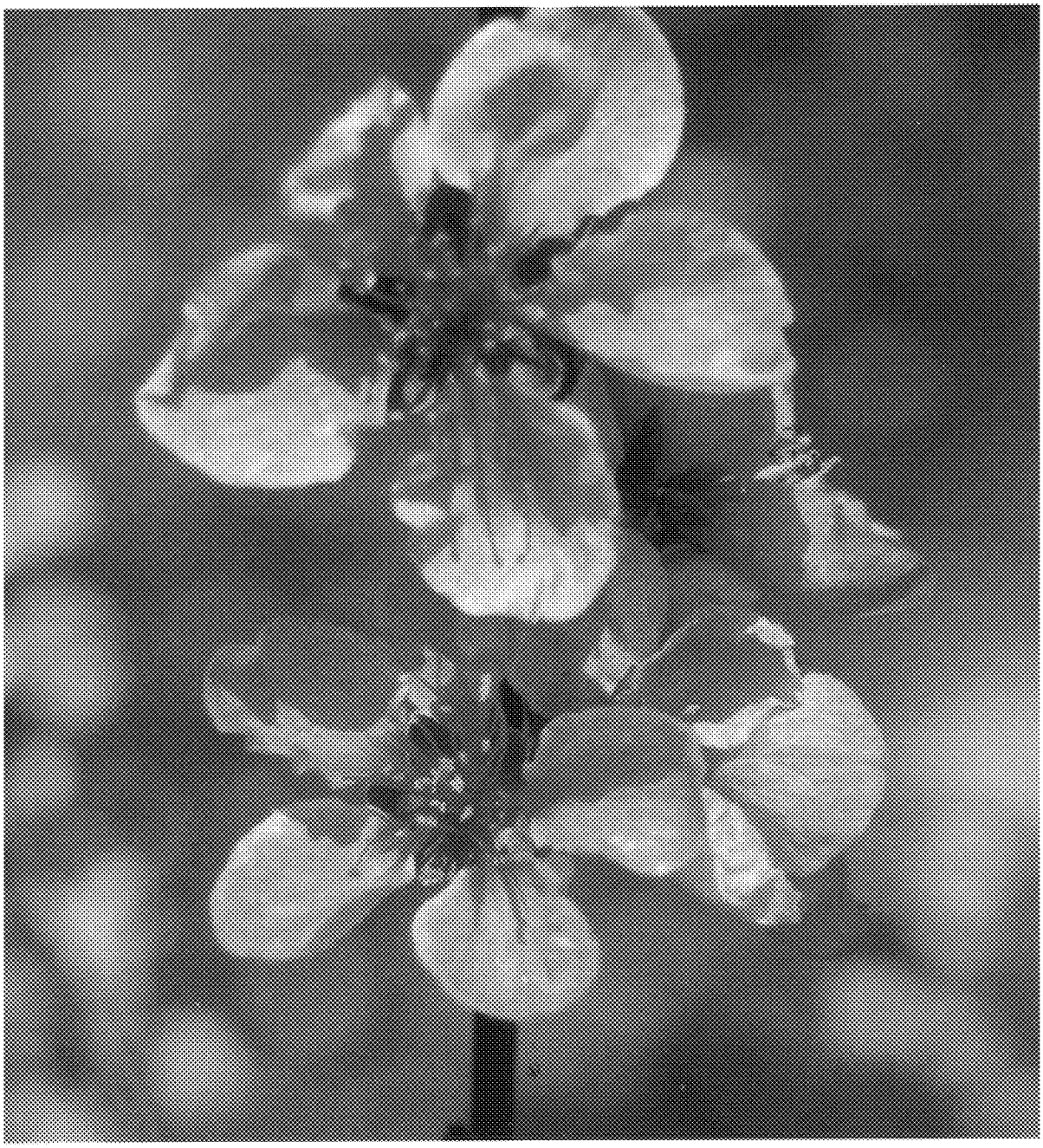
FIG. 4 illustrates the bloom of the new variety at maturity.

A detailed description of the 'FA 42' cultivar follows using The Royal Horticultural Society of London Colour Chart for color identification except where general color terms are sufficient.

Parentage: 'Autumnglo'×'Fayette'.

Locality of the original discovery and observations: Coloma, Berrien County, Mich.

Tree:

*Age of specimen.*—5 years.

*Height.*—3 M.

*Width.*—4 M.

*Vigor.*—Quite vigorous under normal growing conditions.

*Average growth per year.*—45 to 65 cm on terminal branches.

*Density.*—Medium open.

*Form.*—Vase shaped, average of 3 major scaffold branches with 12 to 14 laterals.

*Production.*—Average for a freestone peach, usually 3 to 4 bushels per tree per year.

*Bearing.*—Annual.

*Disease resistance.*—Moderate susceptibility to Bacterial Spot, (*Xanthomonas campestris*) and peach canker (*Cytospora leucostoma* and *Cytospora cincta*). Both have been seen in test plantings. No specific testing for disease susceptibility has been preformed.

*Cold hardiness.*—Quite hardy, hardier than Redhaven, winter bud hardiness threshold averages −14° to −16° F., winter wood hardiness threshold averages −18° to −20° F.

Trunk:

*Size.*—12.5 cm at 15 cm above ground level.

*Surface.*—Smooth with rough vertical striations and horizontal lenticels.

*Lenticels.*—Length 12 to 15 mm, width 1 mm, color Grayed Orange 167A.

*Striations.*—Length 8 to 10 mm, width 0.5 mm, color Grayed White 156D.

1 year branches: Surface smooth, length 45 to 65 cm, diameter 1 mm, color Grayed Orange 167A, average angle to 2-year branch 50°.

2 year branches: Surface smooth, length 45 to 60 mm, diameter 7 mm, color Grayed Orange 175C, average angle to 3-year branch 45°.

3 year branches: Smooth surface, length 220 cm, diameter 10 mm, color Grayed Orange 177C, average angle to 4 year scaffold 45°.

3 year lenticels: Length 1.5 mm, width 0.5 mm, color Grayed Orange 167D.

4 year scaffolds: Slightly rough surface, diameter 12 mm, color Grayed Orange 167B.

4 year lenticels: Length 6 mm, width 0.75 mm, color Grayed Orange 167B.

Leaf buds:

*Size.*—Dormant length 2 mm, width 1 mm.

*Bud scale color (dormant).*—Grayed Orange 178B, bud tip color Grayed White 156A.

*Placement.*—Tightly applied to branch.

*Internode distance.*—22 mm.

Leaves:

*Size.*—Length 85 mm, width 18 mm at widest point.

*Form.*—Lanceolate, tip sharply pointed.

*Thickness.*—Medium thin.

*Texture.*—Smooth, non-pubescent.

*Margin.*—Roundly crenate.

*Adaxile leaf surface.*—Yellow Green 146A.

*Abaxile leaf surface.*—Yellow Green 146B.

*Veination.*—Alternate, adaxial midvein color Yellow Green 153A, adaxial midvein color Yellow Green 158B.

*Petiole.*—Length 5 to 6 mm, width 1.3 mm.

*Petiole groove.*—Depth 0.1 mm, extending entire length of petiole.

*Glands.*—Reniform, 5 to 9 on the base of most leaves. Generally located on the upper petiole, occasionally on the lower leaf.

*Gland color.*—Red Purple 59B.

Flowers:

*Bloom period.*—April 20 to April 25 in Coloma, Van Buren County, Mich.

*Duration of bloom.*—7–10 days, dependent on weather conditions.

*Pollination requirements.*—Self fertile.

*Presentation.*—Showy.

*Fragrance.*—Faint.

*Pollen.*—Present.

*Bud.*—Length: 20–22 mm. Diameter: 4–6 mm. Color: Red Purple 68A to Red Purple 67C.

*Flowers at full bloom.*—Corolla Diameter: 38 to 40 mm. Numbers of Flowers per Cluster: Single. Petals: Arrangement: 5 in number, separate. Adaxile Color: Red Purple 68B. Abaxile Color: Red Purple 67C. Shape: Oval, cupped. Margin: slightly ruffled. Base: Bluntly pointed. Apex: Rounded. Size: Length 17 mm, width 12 mm. Texture: Soft. Peduncle: Length 2 mm, color Yellow Green 145A. Pedicel: Cone shaped, length 7 mm, 2 mm in width at base, 5 mm in width at receptacle. Pedicel Color: Yellow Green 145A at base changing to Grayed Red 186A at receptacle. Sepals: 5 in number, adaxial color Grayed Red 182B, abaxial color Gray Red 182A. Filaments: length 9 to 11 mm, color Red Purple 68B. Anthers: Held slightly below corolla, color Grayed Yellow 161A. Ovary: Length 16 mm, color Yellow Green 145D. Style: Length 15 mm, width 2 mm, color Yellow Green 145D. Stigma: Width 0.8 mm, color Grayed Yellow 161A.

Fruit:

*Maturity when described.*—Shipping ripe.

*Date of first picking.*—September 24, 45 days after 'Redhaven', 7 days after 'Fayette', 2 days after 'Laurol'.

*Date of last picking.*—September 30, may vary by 2 to 3 days due to temperature.

*Size.*—Large, diameter 80–100 mm, length 70–90 mm.

*Form.*—Round, even shoulders, slight bulge on pistil point, tip flat to slightly indented.

*Stem cavity.*—5 mm deep, 9 mm wide, stem abscises cleanly.

Skin:

*Thickness.*—Medium.

*Texture.*—Very slightly pubescent, somewhat resistant to puncture.

*Tendency to crack.*—Very slight.

*Color.*—Dark red blush of Red 53A on 75 to 80% of the surface, middle blush of Red 47B, background color of yellow 11A.

*Flavor.*—Good, non-bitter.

*Pubescence.*—Slight.

Flesh:

*Texture.*—Firm, dense, melting.

*Acidity.*—Medium high.

*Flavor.*—Excellent, very good acid/sugar balance.

*Aroma.*—Very high.

*Fibers.*—Few, very fine.

*Color.*—Clear, Yellow 11C, non-browning.

*Coloration at the pit.*—Red 46A at interface with pit bleeding to Red 47B in the flesh. Depth of coloring into the flesh 1.5 to 2 mm.

*Eating quality.*—Excellent.

Stone:

*Size.*—Length 16 mm, width 11 mm.

*Form.*—Elongated, elliptical with a prominent tip.

*Apex.*—Sharply pointed, point extends 2.5 mm from body of stone.

*Sides.*—Even.

*Base.*—Flat, slightly tilted at abscission layer with stem.

*Surface.*—Deeply furrowed.

*Dorsal groove margin.*—Clean, slightly raised.

*Color.*—Grayed Orange 165A.

*Kernel.*—Length 8 mm, width 4 mm, color Grayed Orange 164A, surface very slightly rough.

*Type.*—Freestone.

*Tendency to crack.*—Slight, may crack under wet, hot, conditions.

Use: Fresh market.

Shipping quality: Excellent, can be graded on a commercial peach grader and shipped via truck.

Keeping quality: Excellent, will store for up to 2 months in common storage with minimal loss of flavor and color.

I claim:

1. A new and distinct variety of peach tree, *Prunus persica,* substantially as herein shown and described, characterized particularly as to novelty by the unique combination of vigorous, regular bearing tree producing freestone fruits having with non-browning flesh and large, round, firm fruits with 75 to 80% blushed red skin color at maturity which occurs 45 days after the maturity of 'Redhaven' peach.

* * * * *